(12) United States Patent
Li et al.

(10) Patent No.: US 10,527,748 B2
(45) Date of Patent: Jan. 7, 2020

(54) NUCLEAR MAGNETIC RESONANCE SENSING DEVICE FOR DOWNHOLE MEASUREMENTS

(71) Applicant: HALLIBURTON ENERGY SERVICES, INC., Houston, TX (US)

(72) Inventors: Lilong Li, Humble, TX (US); Songhua Chen, Katy, TX (US); Arcady Reiderman, Katy, TX (US)

(73) Assignee: Halliburton Energy Services, Inc., Houston, TX (US)

(*) Notice: Subject to any disclaimer, the term of this patent is extended or adjusted under 35 U.S.C. 154(b) by 32 days.

(21) Appl. No.: 15/541,276

(22) PCT Filed: Aug. 8, 2016

(86) PCT No.: PCT/US2016/046074
§ 371 (c)(1),
(2) Date: Jun. 30, 2017

(87) PCT Pub. No.: WO2018/030992
PCT Pub. Date: Feb. 15, 2018

(65) Prior Publication Data
US 2018/0267197 A1     Sep. 20, 2018

(51) Int. Cl.
*G01V 3/32* (2006.01)
*E21B 49/08* (2006.01)
*G01N 24/08* (2006.01)
*E21B 49/00* (2006.01)

(52) U.S. Cl.
CPC .............. *G01V 3/32* (2013.01); *E21B 49/00* (2013.01); *E21B 49/08* (2013.01); *G01N 24/081* (2013.01)

(58) Field of Classification Search
None
See application file for complete search history.

(56) References Cited

U.S. PATENT DOCUMENTS

| 8,471,559 B2 | 6/2013 | Taherian et al. |
| 8,720,552 B2 | 5/2014 | Ayan et al. |
| 9,051,822 B2 | 6/2015 | Ayan et al. |

(Continued)

FOREIGN PATENT DOCUMENTS

WO    2015072985 A1    5/2015

OTHER PUBLICATIONS

International Search Report and Written Opinion dated Apr. 19, 2017, for PCT Application No. PCT/US2016/046074 filed on Aug. 8, 2016. (15 pages).

*Primary Examiner* — Jermele M Hollington
*Assistant Examiner* — Suresh K Rajaputra
(74) *Attorney, Agent, or Firm* — Chamberlain Hrdlicka (57) ABSTRACT

A nuclear magnetic resonance device for subterranean characterization includes a tool body, a peripheral measurement device, and a controller. The tool body includes a permanent magnet located therein, permanent magnet inducing a static magnetic field ($B_0$) in a region of interest. The peripheral measurement device is coupled to the tool body. The measurement device includes a radio frequency coil controllable to generate a radio frequency magnetic field ($B_1$) in the region of interest, receive a response signal, or both. The controller is communicatively coupled to the radio frequency coil and controllable to drive the radio frequency coil, process the response signal, or both.

20 Claims, 7 Drawing Sheets

(56) References Cited

U.S. PATENT DOCUMENTS

| | | | |
|---|---|---|---|
| 2005/0030021 A1* | 2/2005 | Prammer | G01N 24/081 |
| | | | 324/303 |
| 2009/0072825 A1 | 3/2009 | Prammer et al. | |
| 2013/0073206 A1 | 3/2013 | Hou et al. | |
| 2013/0093422 A1 | 4/2013 | Morys et al. | |
| 2015/0054503 A1* | 2/2015 | Chen | E21B 17/1021 |
| | | | 324/303 |
| 2015/0061665 A1* | 3/2015 | Reiderman | G01V 3/32 |
| | | | 324/303 |

* cited by examiner

NUCLEAR MAGNETIC RESONANCE SENSING DEVICE FOR DOWNHOLE MEASUREMENTS

BACKGROUND

Various types of formation and fluid evaluations are performed on oil and gas well before and during production operations. One type of formation evaluation is nuclear magnetic resonance (NMR) logging. NMR logging, a subcategory of electromagnetic logging, measures the induced magnet moment of hydrogen nuclei (protons) contained within the fluid-filled pore space of a formation. NMR can be used to measure the volume, composition, viscosity, and distribution of these fluids, for example. NMR logging is typically performed by specialized NMR logging tools.

NMR logging tools typically include a pad mechanism that is placed close to a wellbore wall to take NMR measurements. The pad typically includes permanent magnets that generate a static magnetic field and an antenna or radio frequency coil for generating an RF magnet field and detecting the NMR data.

BRIEF DESCRIPTION OF THE DRAWINGS

For a detailed description of the embodiments of the invention, reference will now be made to the accompanying drawings in which.

DETAILED DESCRIPTION

Figure 1A:
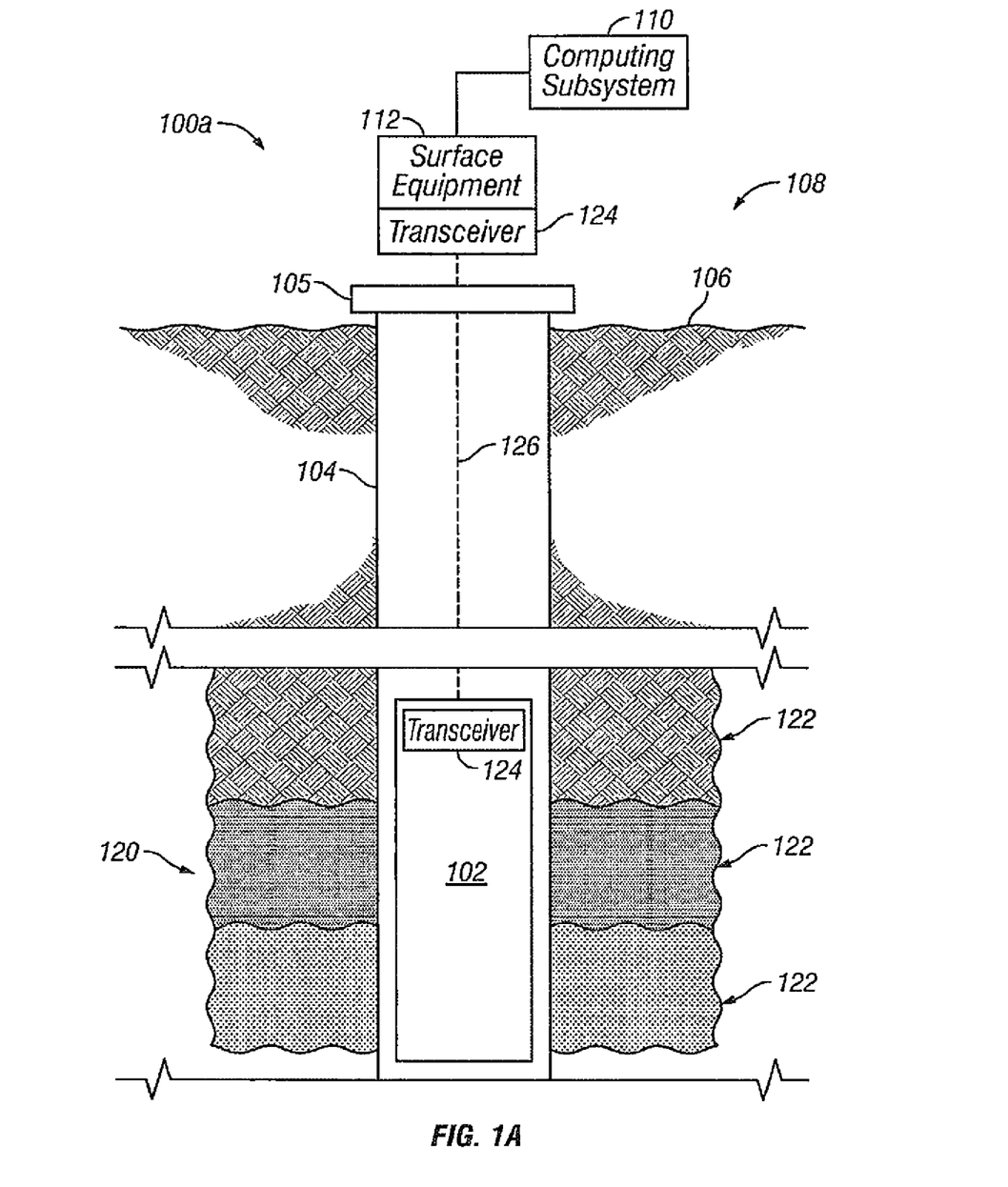
FIG. 1A is a schematic elevation view of an example nuclear magnetic resonance (NMR) logging operation in a well system, in accordance with example embodiments.

FIG. 1A is a schematically-drawn elevation view of an example NMR logging operation 100a. The example NMR logging operation 100a utilizes an NMR logging system 108 in a subterranean region 120 beneath the ground surface 106. An NMR logging operation can include additional or different features that are not shown in FIG. 1A. For example, the NMR logging operation 100a may also utilize additional drilling system components, wireline logging system components, etc.

The subterranean region 120 can include all or part of one or more subterranean formations or zones. The example subterranean region 120 shown in FIG. 1A includes multiple subsurface layers 122 and a wellbore 104 penetrated through the subsurface layers 122. The subsurface layers 122 can include sedimentary layers, rock layers, sand layers, or combinations of these and other types of subsurface layers. One or more of the subsurface layers can contain fluids, such as brine, oil, gas, etc. Although the example wellbore 104 shown in FIG. 1A is drawn as a vertical wellbore, the NMR logging system 108 can be used with vertical wellbores, horizontal wellbores, slant wellbores, curved wellbores, or combinations of these.

The example NMR logging system 108 includes a logging tool 102, surface equipment 112, and a computing subsystem 110 configured to control various aspects of the logging tool 102 and/or receive data therefrom. In the example shown in FIG. 1A, the logging tool 102 is a downhole logging tool that operates while disposed in the wellbore 104. The example surface equipment 112 shown in FIG. 1A operates at or above the surface 106, for example, near the well head 105, to control the logging tool 102 and possibly other downhole equipment or other components of the well system 100. The example computing subsystem 110 can receive and analyze logging data from the logging tool 102. An NMR logging system can include additional or different features, and the features of an NMR logging system can be arranged and operated as represented in FIG. 1A or in another manner.

In some instances, all or part of the computing subsystem 110 can be implemented as a component of, or can be integrated with one or more components of, the surface equipment 112, the logging tool 102, or both. In some cases, the computing subsystem 110 can be implemented as one or more computing structures separate from but communicative with the surface equipment 112 and the logging tool 102.

In some implementations, the computing subsystem 110 is embedded in the logging tool 102, and the computing subsystem 110 and the logging tool 102 can operate concurrently while disposed in the wellbore 104. For example, although the computing subsystem 110 is shown above the surface 106 in the example shown in FIG. 1A, all or part of the computing subsystem 110 may reside below the surface 106, for example, at or near the location of the logging tool 102.

The NMR logging system 108 can include communication or telemetry equipment that allow communication among the computing subsystem 110, the logging tool 102, and other components of the NMR logging system 108. For example, the logging tool 102 and surface equipment 112 can each include one or more transceivers 124 or similar apparatus for wired or wireless data communication among the various components. The NMR logging system 108 can include a communication channel 126 such as systems and apparatus for wireline telemetry, wired pipe telemetry, mud pulse telemetry, acoustic telemetry, electromagnetic telemetry, or a combination of these and other types of telemetry. In some embodiments, the logging tool 102 receives commands, status signals, or other types of information from the computing subsystem 110 or another source via the transceivers 124 and communication channel 126. In some cases, the computing subsystem 110 receives logging data, status signals, or other types of information from the logging tool 102 or another source.

NMR logging operations can be performed in connection with various types of downhole operations at various stages in the lifetime of a well system. Structural attributes and components of the surface equipment 112 and logging tool 102 can be adapted for various types of NMR logging operations. For example, NMR logging may be performed during drilling operations, during wireline logging operations, or in other contexts. As such, the surface equipment 112 and the logging tool 102 may include, or may operate in connection with drilling equipment, wireline logging equipment, or other equipment for other types of operations.

Figure 1B:
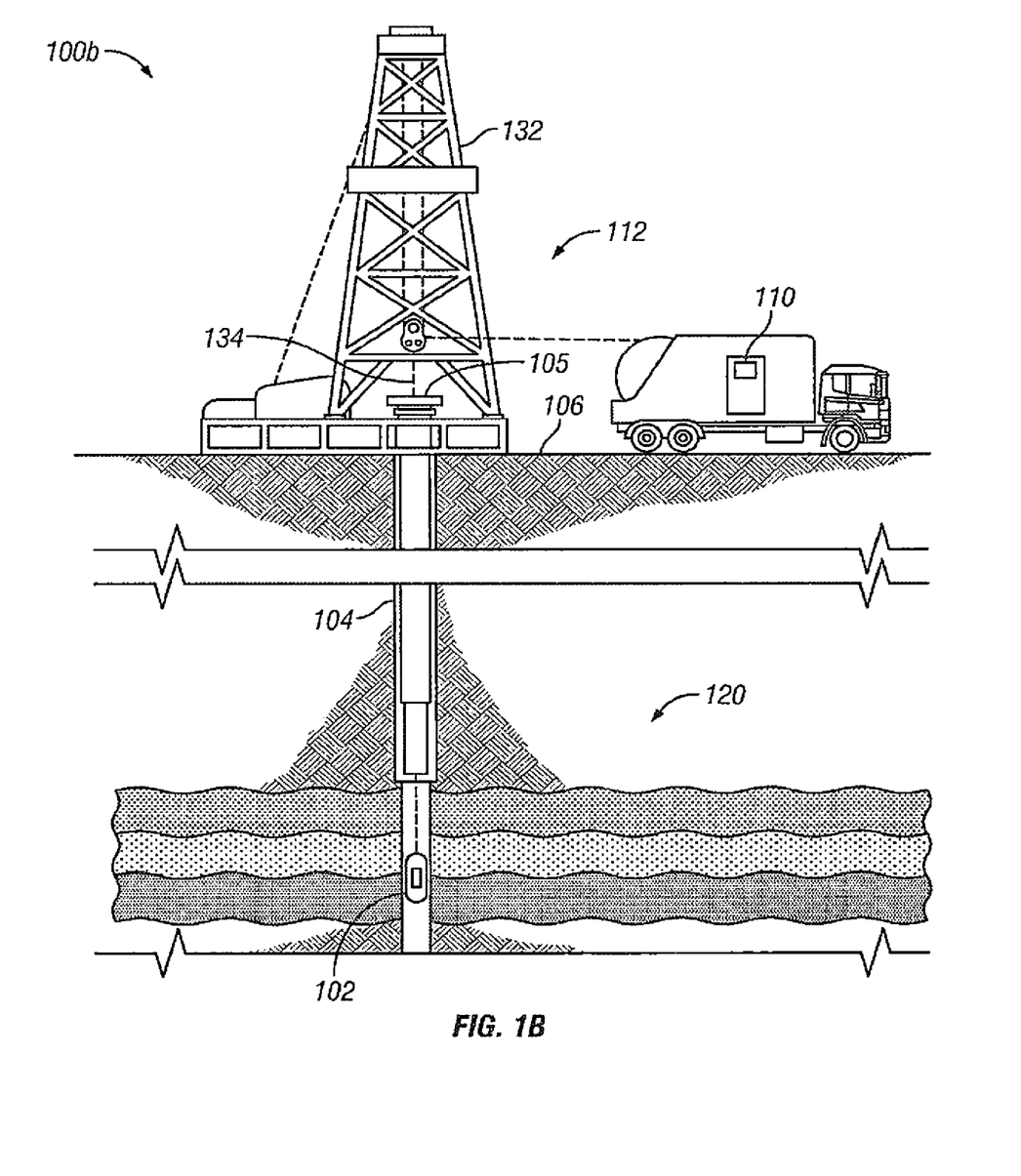
FIG. 1B is a schematic elevation view of a wireline NMR logging system deployed in a well system, in accordance with example embodiments.

In some examples, NMR logging operations are performed during wireline logging operations. FIG. 1B shows an example well system 100b that includes the NMR logging tool 102 in a wireline logging environment. In some example wireline logging operations, the surface equipment 112 includes a platform above the surface 106 equipped with a derrick 132 that supports a wireline cable 134 that extends into the wellbore 104. Wireline logging operations can be performed, for example, after a drill string is removed from the wellbore 104, to allow the wireline logging tool 102 to be lowered by wireline or logging cable into the wellbore 104.

Figure 1C:
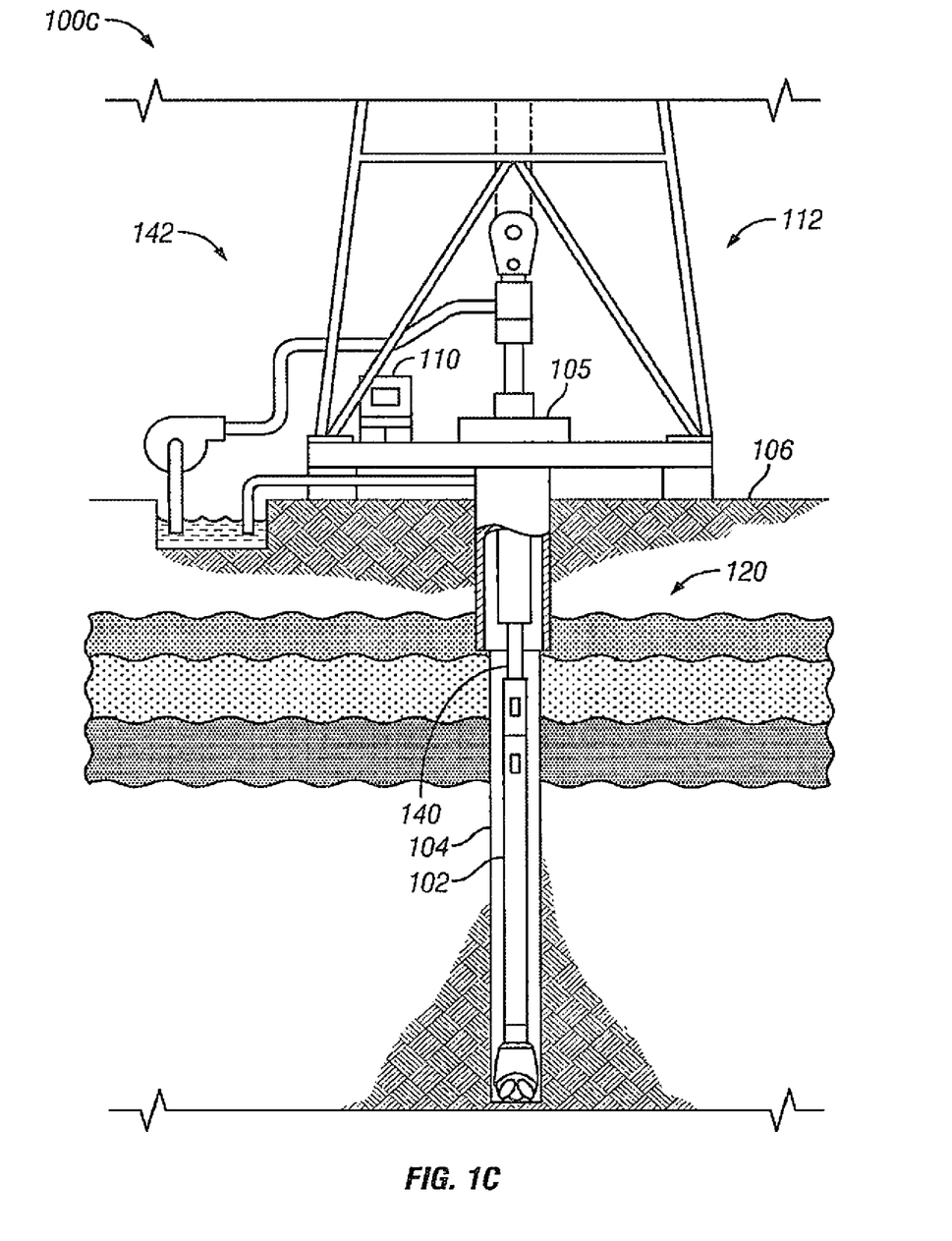
FIG. 1C is a schematic diagram an NMR logging tool in a logging while drilling (LWD) environment, in accordance with example embodiments.

In some examples, NMR logging operations are performed during drilling operations. FIG. 1C shows an example well system 100c that includes the NMR logging tool 102 in a logging while drilling (LWD) environment. Drilling is commonly carried out using a string of drill pipes connected together to form a drill string 140 that is lowered through a rotary table into the wellbore 104. In some cases, a drilling rig 142 at the surface 106 supports the drill string 140, as the drill string 140 is operated to drill a wellbore penetrating the subterranean region 120. The drill string 140 may include, for example, drill pipe, a bottom hole assembly, and other components. The bottom hole assembly on the drill string may include drill collars, drill bits, the logging tool 102, and other components. The logging tools may include measuring while drilling (MWD) tools, LWD tools, and others.

In some example implementations, the logging tool 102 includes an NMR tool for obtaining NMR measurements from the subterranean region 120. As shown, for example, in FIG. 1B, the logging tool 102 can be suspended in the wellbore 104 by a coiled tubing, wireline cable, or another structure that connects the tool to a surface control unit or other components of the surface equipment 112. In some example implementations, the logging tool 102 is lowered to the bottom of a region of interest and subsequently pulled upward (e.g., at a substantially constant speed) through the region of interest. As shown, for example, in FIG. 1C, the logging tool 102 can be deployed in the wellbore 104 on jointed drill pipe, hard wired drill pipe, or other deployment hardware. In some example implementations, the logging tool 102 collects data during drilling operations as it moves downward through the region of interest. In some example implementations, the logging tool 102 collects data while the drill string 140 is moving, for example, while it is being tripped in or tripped out of the wellbore 104.

In some implementations, the logging tool 102 collects data at discrete logging points in the wellbore 104. For example, the logging tool 102 can move upward or downward incrementally to each logging point at a series of depths in the wellbore 104. At each logging point, instruments in the logging tool 102 perform measurements on the subterranean region 120. The measurement data can be communicated to the computing subsystem 110 for storage, processing, and analysis. Such data may be gathered and analyzed during drilling operations (e.g., during logging while drilling (LWD) operations), during wireline logging operations, or during other types of activities.

The computing subsystem 110 can receive and analyze the measurement data from the logging tool 102 to detect properties of various subsurface layers 122. For example, the computing subsystem 110 can identify the density, material content, or other properties of the subsurface layers 122 based on the NMR measurements acquired by the logging tool 102 in the wellbore 104.

In some implementations, the logging tool 102 obtains NMR signals by polarizing nuclear spins in the formation 120 and pulsing the nuclei with a radio frequency (RF) magnetic field. Various pulse sequences (i.e., series of radio frequency pulses, delays, and other operations) can be used to obtain NMR signals, including the Carr Purcell Meiboom Gill (CPMG) sequence (in which the spins are first tipped using a tipping pulse followed by a series of refocusing pulses), the Optimized Refocusing Pulse Sequence (ORPS) in which the refocusing pulses are less than 180°, a saturation recovery pulse sequence, and other pulse sequences.

Figure 2:
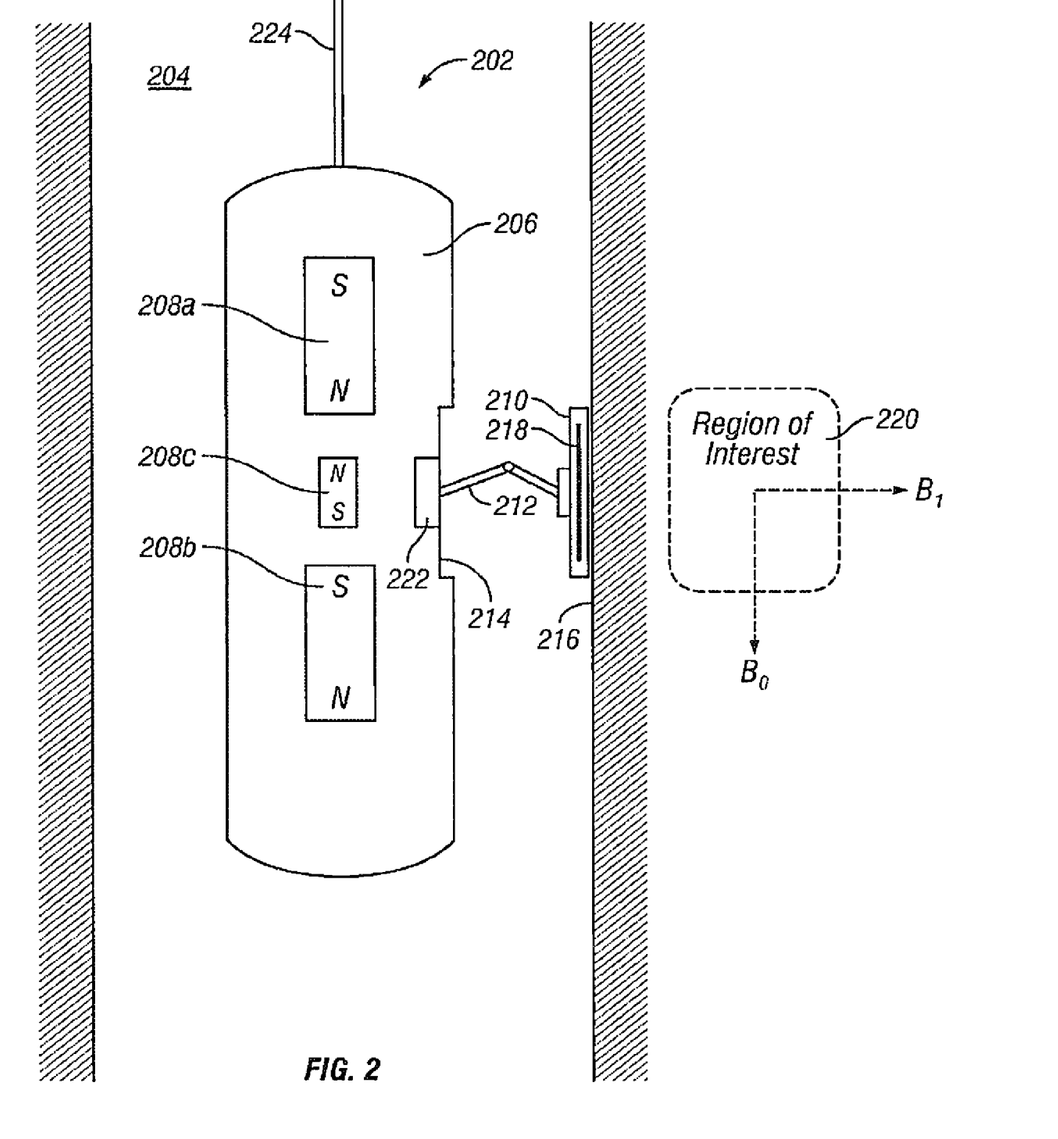
FIG. 2 is a cross-sectional diagram of an NMR logging tool deployed a well 204, in accordance with example embodiments.

FIG. 2 depicts a cross-sectional diagram of an NMR logging tool 200 deployed downhole within a well 204 via a wireline 224, in accordance with one or more embodiments. This example embodiment features a wireline application of the NMR logging tool 200, but the NMR logging 200 may also be a part of a drilling assembly as discussed above. The tool 200 includes a tool body 206 and a peripheral and/or extendable measurement device 210. One or a plurality of magnets 208 may be located within or on the tool body 206, such as magnets 208a-c. The magnets 208 are located external to the measurement device 210 and in some embodiments, the magnets 208 are permanent magnets.

The configuration of magnets 208 in the tool 200 illustrated in FIG. 2 is an example configuration, designed to generate a specific magnetic field shape appropriate for a specific application. However, the magnets 208 can be positioned in any other orientation, with different polarity orientations, sizes, shapes, positioning. There may also be more or fewer magnets 208 than illustrated in FIG. 2. Placement of the magnets inside the tool body rather than in the measurement device 210 allows for a wider range of magnet configurations, which allows for more customizable and desirable static magnetic field shapes.

The measurement device 210 may include a pad extendable from the tool body 206 and may comprise any suitable shape. In some embodiments, the measurement device 210 may be mechanically coupled to the tool body 206 via an extendable arm 212 or any type of extension mechanism, such as but not limited to a telescoping arm or scissor extension, among others.

In one or more embodiments, the measurement device 210 may be stored in a recessed portion 214 of the tool body 206 when in a retracted position. The measurement device 210 may be located anywhere around or on the tool body 206, such as below, above, on the side of, and the like. The measurement device 210 can be extended from the tool body 206 into an extended position to be close to or in contact with the well wall 216, as illustrated in FIG. 2. In one or more embodiments, the measurement device 210 may be extendable to various distances, so as to accommodate wellbores 204 of different sizes and/or better adjust the position of the measurement device 210 with respect to the well wall 216.

The measurement device 210 includes an antenna or radio frequency (RF) coil 218 configured to emit NMR signals. The coil 218 may be located on a surface of the measurement device 210 or embedded within the measurement device 210.

Figure 3:
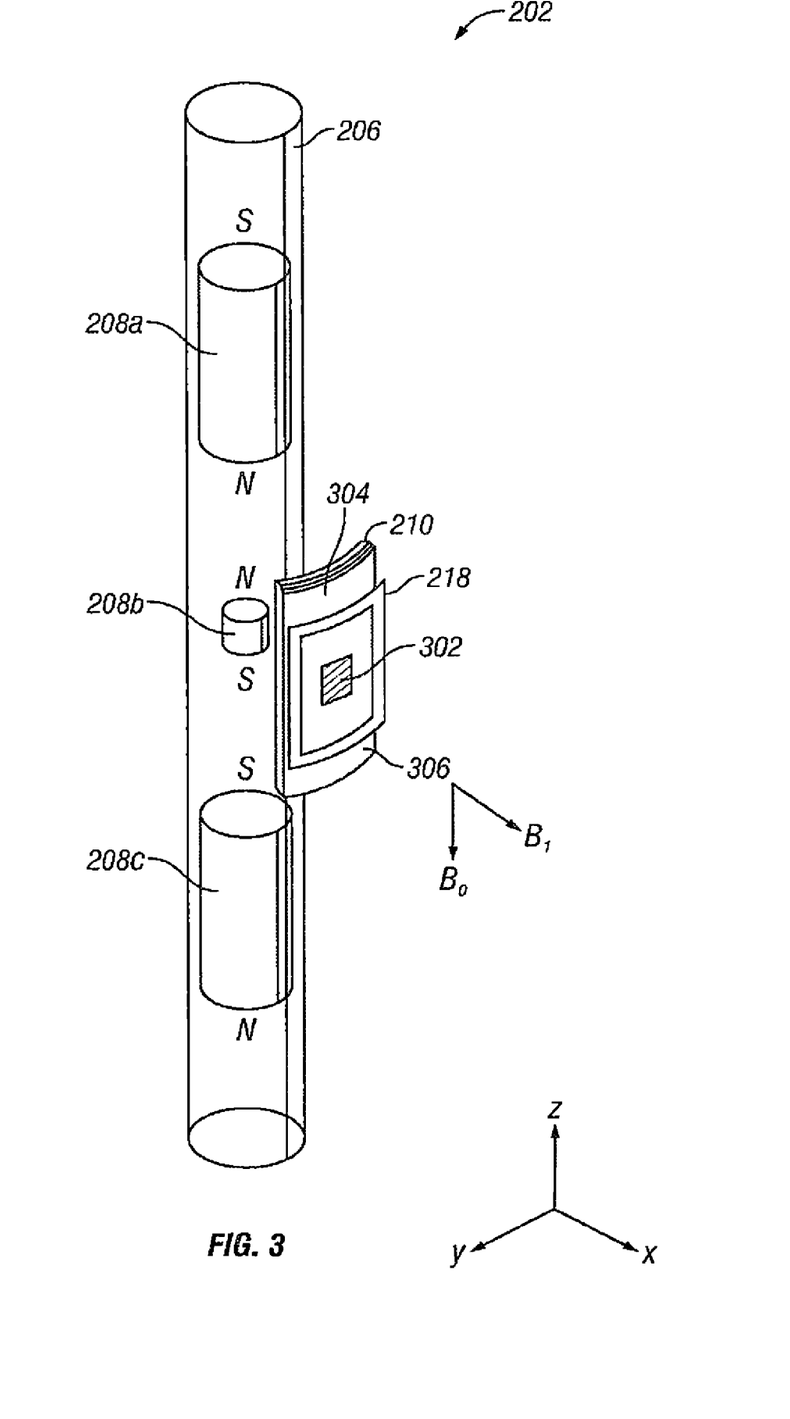
FIG. 3 is a perspective view of the NMR logging tool, in accordance with example embodiments.
Figure 5:
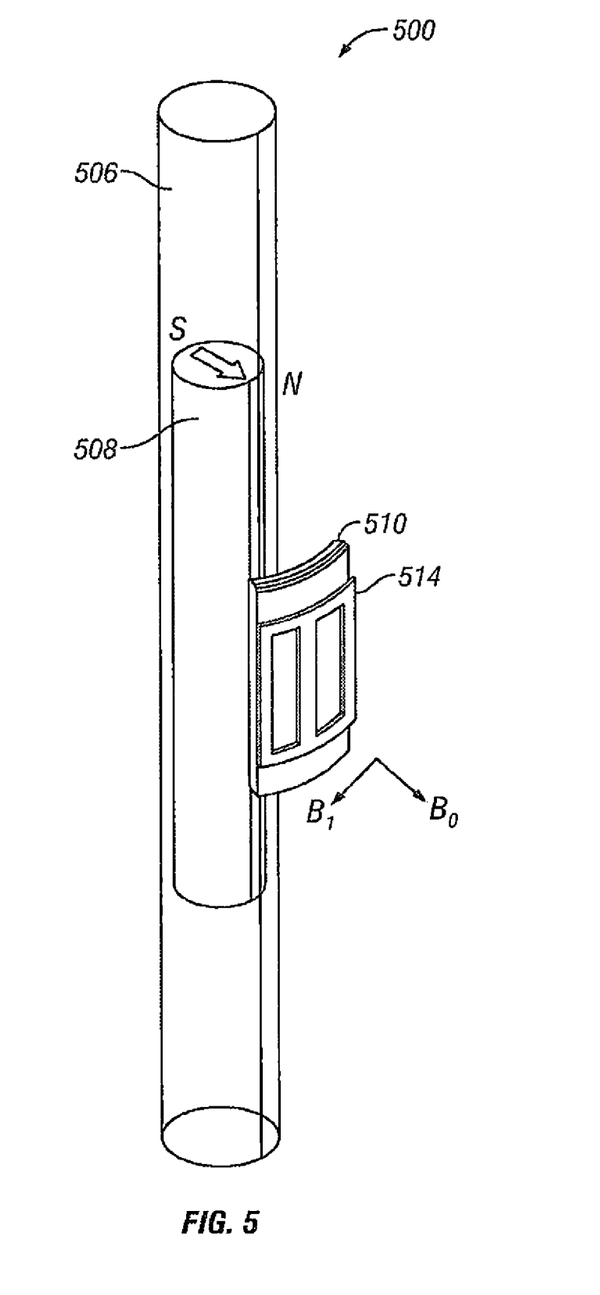
FIG. 5 is a perspective view of yet another embodiment of an NMR logging tool, in accordance with example embodiments.
Figure 6:
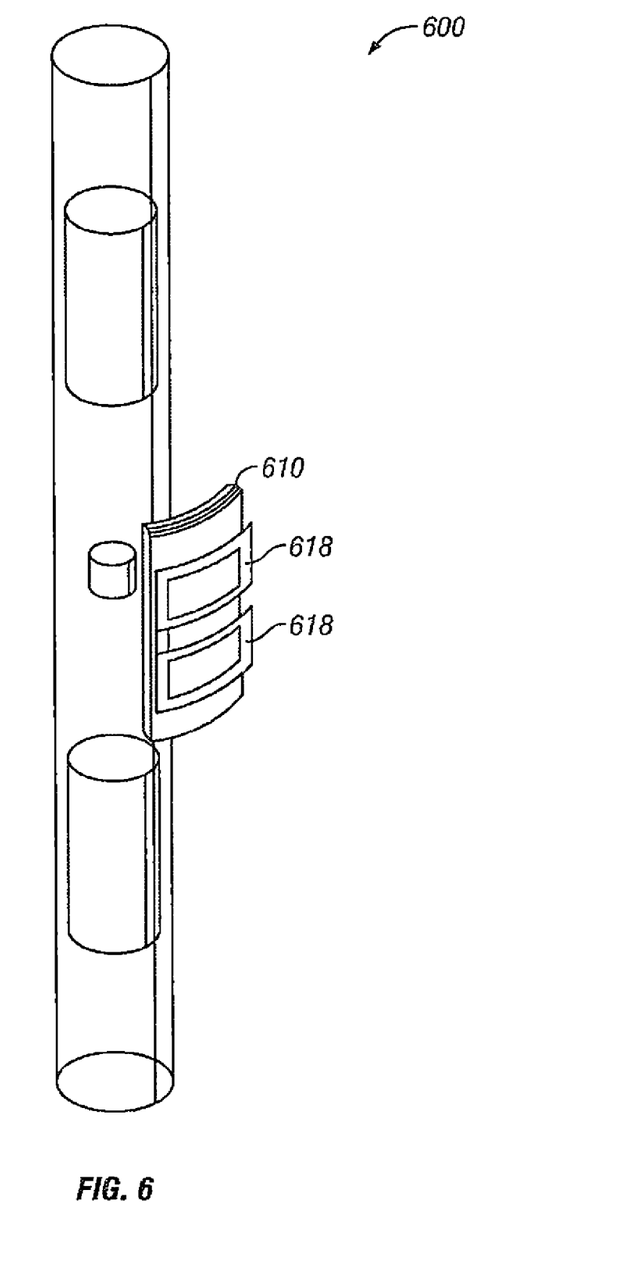
FIG. 6 is a perspective view of yet another embodiment of an NMR logging tool, in accordance with example embodiments.

During an NMR measurement operation, the tool 200 is brought into a position within the well 204 approximate to a region of interest 220 in the surrounding formation. The magnets 208 are positioned to generate a magnetic field, $B_0$, in the region of interest 220. The coil 218 in the measurement device 210 is driven to generate a radio frequency magnetic field, $B_1$, in the region of interest 220. In some embodiments, $B_0$ and $B_1$ are substantially orthogonal in the region of interest 220. In some embodiments, the measurement device 210 may also include strategically placed soft magnetic material, which is a material that is easily magnetized and demagnetized to further enhance and shape the magnetic field, $B_0$ to the desired shape. The combined $B_0$ and $B_1$ field cause polarizing nuclear spins in the formation, which, in some embodiments, is sensed by the RF coil 218, constituting NMR logging data. In some other embodiments, the nuclear spins are sensed by a separate RF coil or detector. The coil 218 may include a radial coil, which produces a radial RF field $B_1$ as illustrated in FIGS. 2 and 3, or a tangential coil which produces a tangential RF field $B_1$ as illustrated in FIG. 5. In one or more embodiments, the coil 218 may include both a radial coil and a tangential coil. As illustrated in the logging tool 600 of FIG. 6, in some embodiments, the measurement device 610 may include more than one coil 618 positioned in any position relative to each other, generating a combined RF field.

The RF coil 218 is electrically coupled to and driven by a controller 222 In one or more embodiments, the controller 222 is located within the tool 200. The controller 222 receives and/or processes NMR data collected by the RF coil 218, and communicates the data uphole. The RF coil 218 can be driven at various adjustable frequencies based on the desired field and pulse scheme. The controller 222 may also be communicatively coupled to the computer subsystem 110 via a communication channel such as a wireline cable, and be powered by a local or above-ground power source via the wireline cable.

FIG. 3 depicts a perspective view of an example of the NMR logging tool 200, which includes the tool body 206, magnets 208, and measurement device 210. The measurement device 210 may have a curved contour 306 for effectively contacting the curved wellbore wall 216. In FIG. 3, the RF coil 218 is coupled to the outer surface 304 of the measurement device 210. The RF coil 218 may be placed in contact with the wellbore wall 216 when the measurement device 210 is in the extended position.

In the embodiment of FIG. 3, the static magnetic field, $B_0$, is substantially in a longitudinal direction (or z direction) and the RF magnetic field, $B_1$, produced by the radial RF coil 218 is substantially transversal and perpendicular to the direction of the static magnetic field, $B_0$. The upper and lower magnets 208a, 208c may be of the same size and shape and configured symmetrically with respect to the plane perpendicular to the axis of the magnet 208b in the middle of the two magnets. Magnets 208a, 208c produce a concavely-shaped static magnetic field isoline in the area of interest 220. In order to match the static magnetic field isoline to the RF field sensitivity as close as possible, a small magnet 208b is placed in the middle to boost the magnetic field, $B_0$, in the middle region and form a static magnetic field, $B_0$, that is substantially directly in front of the RF coil window. The shapes of the magnets 208 are not limited to cylinders. For example, ring shaped magnets can be used if space is needed for other components.

Figure 4:
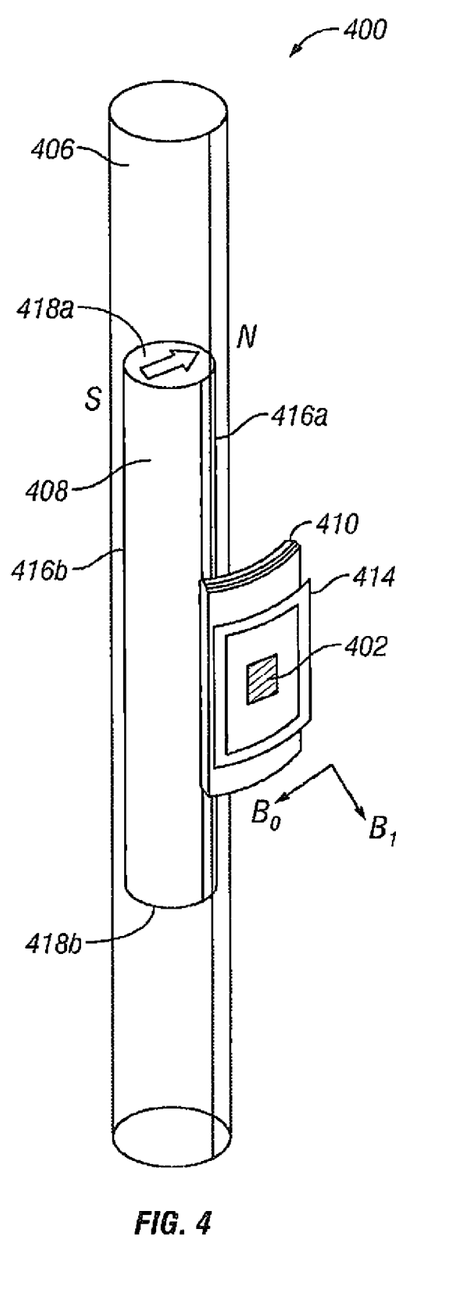
FIG. 4 is a perspective view of another embodiment of an NMR logging tool, in accordance with example embodiments.

FIG. 4 depicts a perspective view of another embodiment of an NMR logging tool 400. The tool 400 includes a tool body 406 having a magnet 408 located therein. In this example embodiment, there is a single long magnet 408 with poles located at its sides 416a, 416b rather than at its ends 418a, 418b. The tool 400 also includes a measurement device 410 with an RF coil 414 similar to that of FIG. 3. In some embodiments, the poles of the magnet 408 are aligned tangentially to the RF coil 414. Such a configuration of the magnet 408 and RF coil 414, which is a radial RF coil 414, can be used to generate a tangential static magnetic field, $B_0$, and a radial RF magnetic field, $B_1$, in an area of interest within a formation. In some embodiments, the measurement device 410 also includes a soft magnet material 402. In certain such embodiment, it may be preferable to create macroscopic anisotropy in the soft magnet material 402 by either creating gaps in the tangential direction, or using an anisotropic material that has substantially lower permeability in the tangential direction.

FIG. 5 depicts a perspective view of another embodiment of an NMR logging tool 500. The tool 500 includes a tool body 506 having a magnet 508 located therein. In this example embodiment, there is a single long magnet 508 with poles located at its sides 516a, 516b rather than at its ends 518a, 518b. The tool 500 also includes a measurement device 510 with an RF coil 514. In some embodiments, the RF coil 514 is a tangential coil and generates a tangential RF magnetic field, $B_1$. The magnet 508 may be oriented such that the poles are aligned orthogonally to the RF coil 514, thus generating a radial static magnetic field, $B_0$.

In addition to the embodiments described above, many examples of specific combinations are within the scope of the disclosure, some of which are detailed below:

Example 1: A nuclear magnetic resonance device for subterranean characterization, comprising:
    a tool body;
    a controller;
    a measurement device coupled to and extendable from the tool body, the measurement device including a radio frequency coil that generates a radio frequency magnetic field ($B_1$) in response to a signal from the controller; and
    a permanent magnet coupled to the tool body and separate from the measurement device, the permanent magnet generating a static magnetic field ($B_0$).

Example 2: The device of claim 1, further comprising a plurality of permanent magnets coupled to the tool body.

Example 3: The device of claim 1, wherein $B_0$ is substantially orthogonal to $B_1$ in a region of interest.

Example 4: The device of claim 1, wherein the tool body is coupled to a wireline.

Example 5: The device of claim 1, wherein the radio frequency coil is controllable to receive a signal produced by nuclear spin induced by $B_0$, $B_1$, or both.

Example 6: The device of claim 1, wherein the measurement device comprises a soft magnetic material.

Example 7: The device of claim 1, wherein the radio frequency coil is drivable at an adjustable frequency and pulse scheme.

Example 8: The device of claim 1, wherein the permanent magnet is located within the tool body.

Example 9: A nuclear magnetic resonance device for subterranean characterization, comprising:
    a tool body comprising a permanent magnet located therein, the permanent magnet inducing a static magnetic field ($B_0$) in a region of interest;
    a peripheral measurement device coupled to the tool body, the measurement device comprising an radio frequency coil is controllable to generate a radio frequency magnetic field (BO in the region of interest, receive a response signal, or both; and a controller communicatively coupled to the radio frequency coil, the controller is controllable to drive the radio frequency coil, process the response signal, or both.

Example 10: The device of claim 9, wherein the measurement device is extendable towards the region of interest.

Example 11: The device of claim 9, wherein the radio frequency coil comprises a radial coil, a tangential coil, or both.

Example 12: The device of claim 9, wherein the radio frequency coil is controllable to deliver nuclear magnetic resonance pulses to the region of interest.

Example 13: The device of claim 9, wherein the measurement device comprises a soft magnetic material.

Example 14: The device of claim 9, wherein $B_0$ is substantially orthogonal to $B_1$ in a region of interest.

Example 15: The device of claim 9, wherein the radio frequency coil is located on a surface of the measurement device or embedded within the measurement device.

Example 16: A method of characterizing a subterranean formation with nuclear magnetic resonance, comprising:
  inducing a static magnetic field ($B_0$) via a permanent magnet coupled to or within a tool body of a nuclear magnetic resonance device;
  generating a radio frequency magnetic field ($B_1$) via a first radio frequency coil located in a measurement device of the nuclear magnetic resonance device; and
  receiving a nuclear magnetic resonance response signal via the radio frequency coil or a second radio frequency coil.

Example 17: The method of claim 16, further comprising driving the radio frequency coil at an adjustable frequency, pulse scheme, or both.

Example 18: The method of claim 16, further comprising moving the nuclear magnetic resonance device into a region of a well approximate to an area of interest.

Example 19: The method of claim 16, further comprising extending the measurement device from the nuclear magnetic resonance device towards a wellbore wall.

Example 20: The method of claim 16, further comprising processing the nuclear magnetic resonance response signal into well characterization data.

This discussion is directed to various embodiments of the invention. The drawing figures are not necessarily to scale. Certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed may be employed separately or in any suitable combination to produce desired results. In addition, one skilled in the art will understand that the description has broad application, and the discussion of any embodiment is meant only to be exemplary of that embodiment, and not intended to intimate that the scope of the disclosure, including the claims, is limited to that embodiment.

Certain terms are used throughout the description and claims to refer to particular features or components. As one skilled in the art will appreciate, different persons may refer to the same feature or component by different names. This document does not intend to distinguish between components or features that differ in name but not function, unless specifically stated. In the discussion and in the claims, the terms "including" and "comprising" are used in an open-ended fashion, and thus should be interpreted to mean "including, but not limited to . . . ." Also, the term "couple" or "couples" is intended to mean either an indirect or direct connection. In addition, the terms "axial" and "axially" generally mean along or parallel to a central axis (e.g., central axis of a body or a port), while the terms "radial" and "radially" generally mean perpendicular to the central axis. The use of "top," "bottom," "above," "below," and variations of these terms is made for convenience, but does not require any particular orientation of the components.

Reference throughout this specification to "one embodiment," "an embodiment," or similar language means that a particular feature, structure, or characteristic described in connection with the embodiment may be included in at least one embodiment of the present disclosure. Thus, appearances of the phrases "in one embodiment," "in an embodiment," and similar language throughout this specification may, but do not necessarily, all refer to the same embodiment.

Although the present invention has been described with respect to specific details, it is not intended that such details should be regarded as limitations on the scope of the invention, except to the extent that they are included in the accompanying claims.

What is claimed is:

1. A nuclear magnetic resonance device for subterranean characterization of a formation and a formation fluid, comprising:
  a tool body;
  a controller;
  a measurement device coupled to and extendable from the tool body, the measurement device including a radio frequency coil that generates a radio frequency magnetic field ($B_1$) in response to a signal from the controller without a permanent magnet; and
  a permanent magnet coupled to the tool body and separate from the measurement device, the permanent magnet generating a static magnetic field ($B_0$) in a magnetic field shape.

2. The device of claim 1, wherein the permanent magnet comprises a transversal dipole magnet and the measurement device comprises a transversal dipole antenna, or the permanent magnet comprises a longitudinal magnet and the measurement device comprises a transversal dipole antenna.

3. The device of claim 1, wherein $B_0$ is substantially orthogonal to $B_1$ in a region of interest.

4. The device of claim 1, wherein the tool body is coupled to a wireline.

5. The device of claim 1, wherein the radio frequency coil is controllable to receive a signal produced by nuclear spin induced by $B_0$, $B_1$, or both.

6. The device of claim 1, wherein the measurement device comprises a soft magnetic material.

7. The device of claim 1, wherein the radio frequency coil is drivable at an adjustable frequency and pulse scheme.

8. The device of claim 1, wherein the permanent magnet is located within the tool body.

9. A nuclear magnetic resonance device for subterranean characterization of a formation and a formation fluid, comprising:
  a tool body comprising a permanent magnet located therein, the permanent magnet inducing a static magnetic field ($B_0$);
  a peripheral measurement device coupled to the tool body, the measurement device comprising a radio frequency coil that is controllable to generate a radio frequency magnetic field ($B_i$) in the region of interest without a permanent magnet in the peripheral measurement device, receive a response signal, or both; and a controller communicatively coupled to the radio frequency coil, the controller is controllable to drive the radio frequency coil, process the response signal, or both.

10. The device of claim 9, wherein the measurement device is extendable towards the region of interest.

11. The device of claim 9, wherein the radio frequency coil comprises a radial coil, a tangential coil, or both.

12. The device of claim 9, wherein the radio frequency coil is controllable to deliver nuclear magnetic resonance pulses to the region of interest.

13. The device of claim 9, wherein the measurement device comprises a soft magnetic material.

14. The device of claim 9, wherein $B_0$ is substantially orthogonal to $B_1$ in a region of interest.

15. The device of claim 9, wherein the radio frequency coil is located on a surface of the measurement device or embedded within the measurement device.

16. A method of characterizing a subterranean formation with nuclear magnetic resonance, comprising:

inducing a static magnetic field ($B_0$) via a permanent magnet coupled to or within a tool body of a nuclear magnetic resonance device, wherein the static field is induced within the tool body and within the subterranean formation;

generating a radio frequency magnetic field ($B_1$) via only a first radio frequency coil located in a measurement device coupled to and extendable from the tool body of the nuclear magnetic resonance device; and receiving a nuclear magnetic resonance response signal via the radio frequency coil or a second radio frequency coil.

17. The method of claim 16, further comprising driving the radio frequency coil at an adjustable frequency, pulse scheme, or both.

18. The method of claim 16, further comprising moving the nuclear magnetic resonance device into a region of a well approximate to an area of interest.

19. The method of claim 16, further comprising extending the measurement device from the nuclear magnetic resonance device towards a wellbore wall.

20. The method of claim 16, further comprising processing the nuclear magnetic resonance response signal into well characterization data.

* * * * *